United States Patent [19]

Biche

[11] 4,202,351
[45] May 13, 1980

[54] IDENTIFICATION MEANS FOR ELECTROCARDIOGRAPHIC MONITORING INSTRUMENTS OR THE LIKE

[75] Inventor: Barton A. Biche, Binghamton, N.Y.

[73] Assignee: Bunker Ramo Corporation, Oak Brook, Ill.

[21] Appl. No.: 929,586

[22] Filed: Jul. 31, 1978

[51] Int. Cl.² ............................................. A61B 5/04
[52] U.S. Cl. ................................... 128/696; 40/316; 339/113 R
[58] Field of Search ........................ 128/696, 639–644; 40/316; 116/278; 339/113 R, 113 L, 128, 148, 150 C, 201, 202, 206 R

[56] References Cited

U.S. PATENT DOCUMENTS

| | | | |
|---|---|---|---|
| 922,576 | 5/1909 | Glauber | 40/2 |
| 1,373,416 | 4/1921 | Everett | 40/2 |
| 1,644,132 | 10/1927 | Horsburgh | 40/2 |
| 1,984,839 | 12/1934 | Murray | 40/2.2 |
| 2,070,952 | 2/1937 | Mitchel | 40/8 |
| 2,592,788 | 4/1952 | Branson | 173/269 |
| 2,629,953 | 3/1953 | von Stackelberg et al. | 40/21 |
| 2,930,155 | 3/1960 | Becker | 40/2 |
| 3,010,743 | 11/1961 | Bengtson, Jr. | 287/53 |
| 3,313,057 | 4/1967 | Leadpy | 40/331 |
| 3,323,514 | 7/1967 | Barret, Jr. | 128/696 |
| 3,410,247 | 11/1968 | Dronberger | 116/133 |
| 3,430,377 | 3/1969 | Ellison | 40/332 |
| 3,542,013 | 11/1970 | Stephenson | 128/696 |
| 3,678,608 | 7/1972 | Minasy | 40/20 R |
| 3,769,933 | 11/1973 | Fox | 116/124.2 X |
| 3,831,549 | 8/1974 | Parsons | 116/124.1 |
| 3,964,470 | 6/1976 | Trombley | 128/642 |
| 3,977,104 | 8/1976 | Stupar | 40/2 R |
| 3,977,105 | 8/1976 | Tscbouch | 40/2.2 |

FOREIGN PATENT DOCUMENTS

1022655 7/1958 Fed. Rep. of Germany .
829731 9/1975 France .

OTHER PUBLICATIONS

Pipberger et al., "American Heart Association," pp. 11, 19 & unnumbered page.

Primary Examiner—William E. Kamm
Attorney, Agent, or Firm—F. M. Arbuckle; J. R. Hoffman

[57] ABSTRACT

An identification means is disclosed for use with lead wires of electrocardiographic monitoring instruments or the like. The identification means includes a terminal body member secured at one end of a lead wire and has a peripheral recess extending substantially thereabout. An identification member having identifying means corresponding to one of a plurality of commonly recorded anatomical positions is positionable onto the terminal body member and has an interior lip snap fit within the recess of the terminal body member to retain the identification member onto the terminal body member and prevent unintentional removal therefrom. The identifying means on the identification member comprises raised indicia and is color coded to the anatomical positions. The identification member exclusive of the raised indicia also is color coded to different color codifications than the raised indicia. A plurality of identification members are provided, each comprising one of a set thereof of differently color coded members. The outer adjacent peripheral surfaces of the identification member and the terminal body member are rounded and flush with each other to preclude any positive gripping means therebetween. In one form of the invention, the terminal body member has a protruding exteriorly threaded portion, and the identification member has an interiorly threaded portion for rotational engagement therewith. The terminal body member has a reduced diameter portion adjacent the inner end of the exteriorly threaded first portion thereof for receiving the interiorly threaded portion of the identification member out of threaded engagement.

26 Claims, 9 Drawing Figures

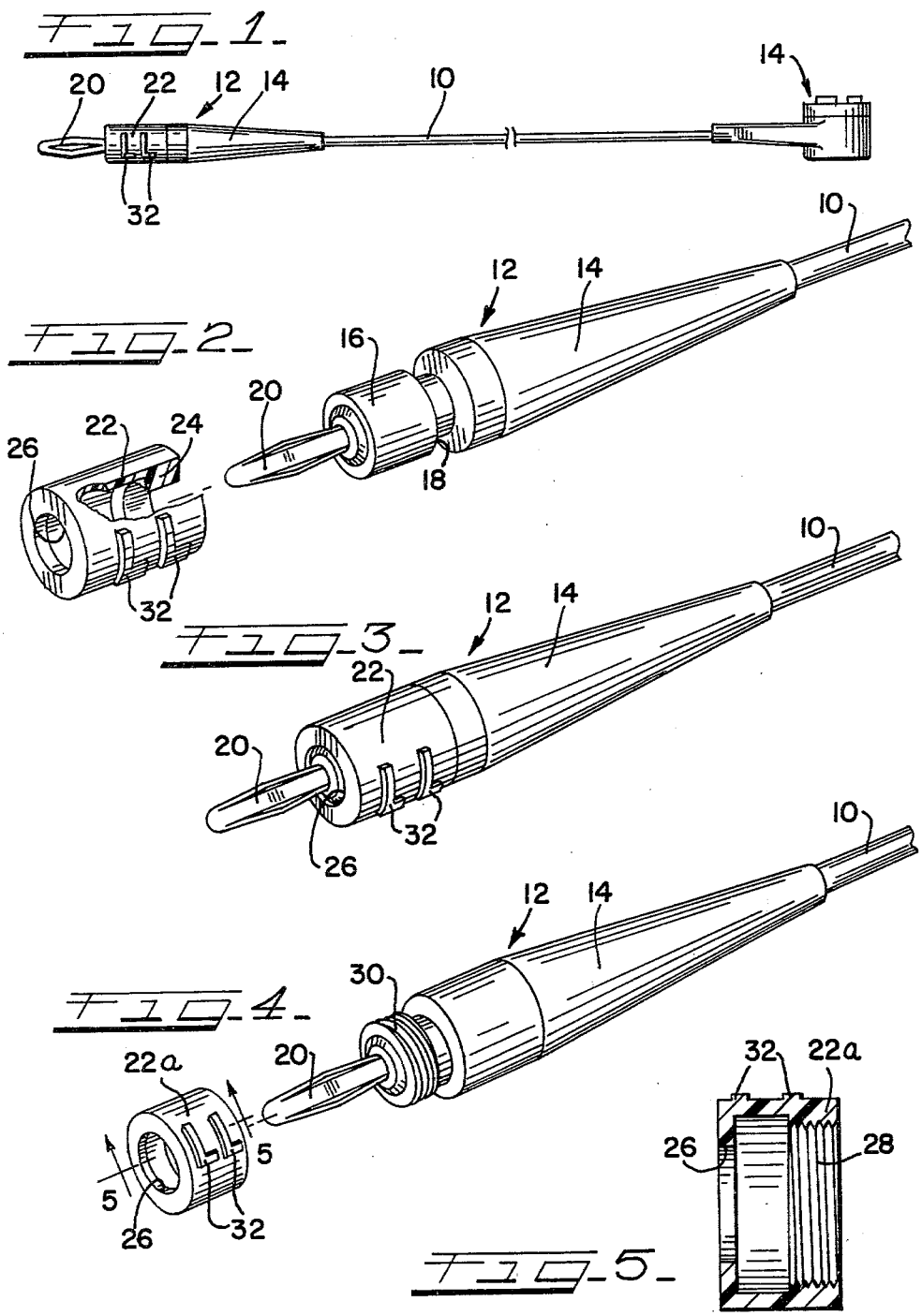

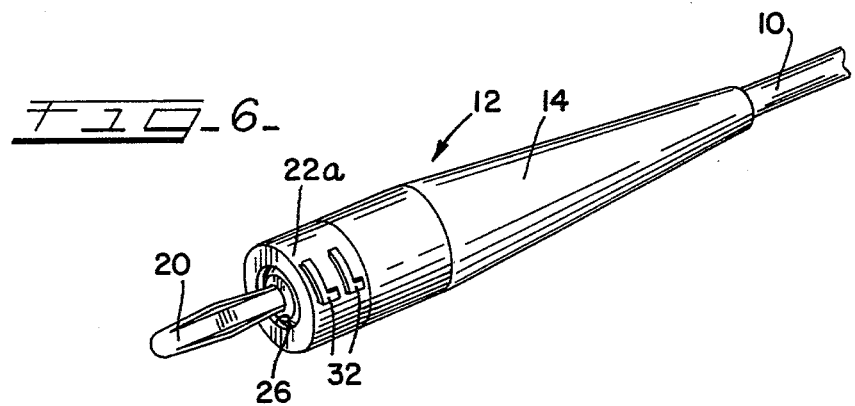
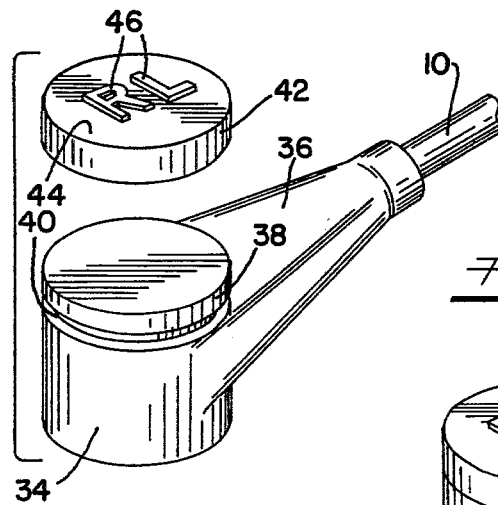
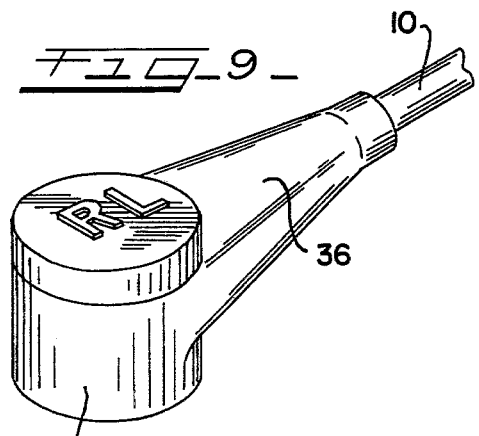
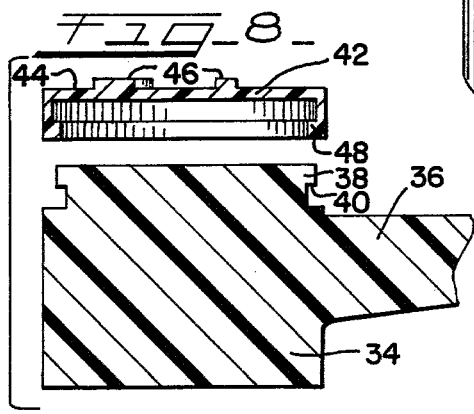

IDENTIFICATION MEANS FOR ELECTROCARDIOGRAPHIC MONITORING INSTRUMENTS OR THE LIKE

BACKGROUND OF THE INVENTION

This invention relates to identification means for the ends of lead wires of electrocardiographic monitoring instruments or the like.

Electrocardiographic monitoring instruments are provided with a plurality of lead wires which comprise output terminals to correspond to each of the commonly recorded anatomical positions; for instance, LA, RA, LL, RL, VI-6, or others, with the lead wires or output terminals associated with the common anatomical positions such as left arm, right arm, left leg, right leg, and particular torso areas. Thus, it can be seen that as many as ten or more lead wires and output terminals are required for each machine. During use, the lead wires require repetitious handling or manipulation for placing onto and off of a patient's body as well as being plugged into and out of the machine itself. Because of this repeated handling of the lead wires, they oftentimes become damaged or broken and must be replaced, requiring a hospital or other user to maintain a considerable supply of replacement wires to insure continuous and immediate usage of the machines. The supply of such an inventory of such lead wires creates problems particularly in view of the fact that the lead wires are labelled, usually by color coding, for each of the plurality of anatomical positions for which the lead wires are utilized in conjunction with the machine itself. The color coding for the patient leads usually is in conformance with uniform colors for electrocardiographs used in the United States and, preferably, world-wide. The color codifications may be associated with either individually colored lead wires or with plug bodies if used at the lead ends.

In the past, the color codifications most often were provided by labeling or cable legends of a permanent type, such as by tags or engraving, for each individual lead wire and, should a lead wire become damaged or broken, a replacement therefor must be obtained from the hospital's inventory corresponding to the particular permanently coded broken lead wire. Readily removable legends or labels are undesirable because of the possible problem of erroneous labeling which would result in an inaccurate reading by the electrocardiographic machine. In addition, environmental problems are caused when using permanent labeling which might be obscured or otherwise made unreadable due to liquids or other materials commonly found around hospitals and the storerooms thereof.

To further exemplify the problems involved in maintaining an inventory of replaceable lead wires for electrocardiographic machines, a present standard or common color coding presently used in the United States might be described. As referred to above, an electrocardiographic machine might include ten lead wires corresponding to the commonly recorded anatomical positions; namely, LA (left arm), RA (right arm), LL (left leg), RL (right leg), and VI-6 (six torso positions). The RL through LA lead wires for the legs and arms would have a base color codification, such as white, and additional color codification for each limb; namely, green for RL, red for LL, white (white on white) for RA, and black for LA. The torso lead wires VI-6 would have a brown base color accompanied by additional indicia relating to the six different torso positions. It can readily be seen that considerable problems result in maintaining an inventory of lead wires for the electrocardiographic machine, particularly when an institutution such as a large hospital might employ a number of such machines. The problems further are enhanced when different machines from different manufacturers are employed which might utilize different types of lead wires or output terminals for the different machines.

This invention is directed to providing identification means for solving these problems in using electrocardiograph monitoring instruments.

SUMMARY OF THE INVENTION

A principal object of this invention is to provide an identification means for the lead wires of electrocardiographic machines of the character described in order to solve the aforementioned problems.

Another object of this invention is to provide identification means for application to and in combination with the ends of lead wires of electrocardiographic monitoring instruments or the like to greatly reduce the number of lead wires required to be maintained in inventory during normal use of such machines when initial selection or replacement of such lead wires are required.

A further object of the invention is to provide identification means of the character described for use on the lead wires of electrocardiographic machines or the like, with the identification means being readily positionally adjustable to facilitate omni-directional reading of the identification means without undue manipulation of the lead wires themselves.

The invention embodied herein is in the form of identification means for application to and in combination with the ends or output terminals of lead wires for electrocardiographic monitoring instruments or the like. Each lead wire has a terminal body member, including a strain relief portion secured at one end of a lead wire and having a circular peripheral recess extending substantially thereabout. An identification member having identifying means corresponding to one of a plurality of commonly recorded anatomical positions is assembled onto the terminal body member. The identification member is sized to be positionable over at least a portion of the terminal body member including the peripheral recess thereof and has an interior lip snap fit within the recess to retain the identification member onto the terminal body member and prevent unintentional removal therefrom. The outer peripheral surface of the identification member and the adjacent outer peripheral surface of the terminal body member are rounded and flush with each other to preclude any positive gripping means therebetween. The circular recess of the terminal body member has a uniform cross-section to provide for relative rotation between the terminal body member and the identification member to facilitate omni-directional reading of the identifying means.

The identifying means on the identification member is color coded to one of a plurality of standard color codifications corresponding to a plurality of anatomical positions, as set forth and described in the preceeding "Background Of The Invention" section herein. The identifying means as disclosed herein comprises raised indicia such as "RL", "LL", "RA", "LA", or "VI-6". The identification member itself exclusive of the raised indicia also is color coded to different color codifications than the raised indicia.

Each individual identification member comprises one of differently color coded identification members corresponding to the above described conventional color coding system.

In one form of the invention, the terminal body member has a protruding exteriorly threaded portion and the identification member has an interiorly threaded portion for threading onto the exteriorly threaded portion of the terminal body member. The terminal body member also provides a reduced diameter portion forming the aforementioned peripheral recess adjacent to the inner end of the exteriorly threaded portion thereof. The reduced diameter portion is adapted to receive the interiorly threaded portion of the identification member out of threaded engagement with the exteriorly threaded portion to further facilitate the prevention of unintentional removal of the identification member as well as to permit free rotation between the terminal body member and the identification member.

As disclosed herein, the identification means of the present invention may be employed on a terminal body member which is adapted for positioning onto the skin of a human anatomy with the lead wire extending outwardly from one side of the body member. The identification member is in the form of a cap having an upwardly facing generally flat surface with the identifying means or raised indicia thereof, the flat surface being in a plane generally parallel to the lead wire. In this form, the outer side surface of the identification cap is flush with the peripheral surface of the terminal body member to preclude any positive gripping means therebetween.

In another form of the invention herein, the identification means is employed on the terminal plug portion of the lead wire, with the terminal body portion including a terminal plug protruding outwardly therefrom and electrically connected to the lead wire. The identification member is in the form of a ring assembled onto the terminal body member with a hole through which the terminal plug protrudes for insertion into the electrocardiographic monitoring instrument.

Other objects, features and advantages of the invention will be apparent from the following detailed description taken in connection with the accompanying drawings.

DESCRIPTION OF THE DRAWINGS

FIG. 1 is a fragmented side elevational view of a lead wire for electrocardiographic monitoring instruments or the like with a terminal plug at one end thereof including the identification means of the present invention and a terminal body member at the other end thereof adapted for positioning onto the skin of a human anatomy;

FIG. 2 is a partially fragmented, exploded perspective view, on an enlarged scale, of the terminal plug end of the lead wire, with the identification ring removed to facilitate the illustration;

FIG. 3 is a perspective view similar to that of FIG. 2 with the identification ring assembled to the terminal plug end of the lead wire;

FIG. 4 is a perspective view similar to that of FIG. 2 showing another form of the invention wherein the identification ring is threaded onto the terminal plug end of the lead wire;

FIG. 5 is a generally vertical section, on an enlarged scale, taken generally along line 5—5 of FIG. 4 through the identification ring shown therein;

FIG. 6 is a perspective view showing the identification ring of FIG. 4 assembled onto the terminal plug end of the lead wire;

FIG. 7 is an exploded perspective view of the end of the lead wire which is adapted for positioning onto a human anatomy, with the identification cap removed to facilitate the illustration;

FIG. 8 is a generally vertical sectional view, on an enlarged scale, of the components shown in FIG. 7; and FIG. 9 is a perspective view showing the identification cap of FIG. 7 in assembled position.

DETAILED DESCRIPTION OF THE INVENTION

Referring to the drawings in greater detail and first to FIG. 1, the identification means of the present invention is shown as applied to or in combination with both ends of a lead wire 10 for an electrocardiographic monitoring instrument or the like which is not shown herein. The identification means is shown employed with the terminal plug end, generally designated 12, as well as the opposite end, generally designated 13, of the lead wire 10. As described herein, the end 13 of the lead is adapted for positioning onto a portion of a human anatomy.

Referring to FIGS. 2 and 3, the terminal plug end 12 of the lead wire 10 includes a terminal body member having a frusto-conical strain relief portion 14, a reduced diameter cylindrical portion 16, and a circular recessed portion 18 which is continuous and of uniform cross-section between the strain relief portion 14 and reduced diameter portion 16. A conductive terminal plug 20 protrudes generally axially outwardly of the reduced diameter portion 16 and is electrically connected to the lead wire 10 for insertion into an appropriate socket in the electrocardiographic machine. The lead wire 10 and the terminal body member which includes the strain relief portion 14, reduced diameter portion 16 and recessed portion 18 preferably are of a neutral color such as gray.

The identification means of the present invention which is utilized with the terminal plug end 12 of the lead wire 10 is in the form of an identification ring 22 which is generally hollow and generally open ended, and which has an interior lip 24 for snap fit within the recess 18 on the terminal body member 12. The end of the identification ring 22 opposite the lip 24 has a hole 26 through which the terminal plug 20 extends when the identification ring is assembled to the terminal body member 12, as shown in FIG. 3. The inner diameter of the identification ring 22 within the lip 24 is slightly smaller than the diameter of the reduced portion 16 of the terminal body member 12 so that the identification ring can be snap fit over the reduced diameter portion 16 until the lip 24 seats within the recess 18. The diameter of the hole 26 in the outside end of the identification ring 22 is smaller than the outside diameter of the reduced portion 16 of the terminal body member 12.

As best seen in FIGS. 1 and 3, the outer peripheral surface of the identification ring 22 and the adjacent outer peripheral surface of the terminal body member 12 are rounded and flush with each other when the identification ring is assembled to the terminal body member to preclude any positive gripping means therebetween so that there can be no unintentional removal of the identification ring. Furthermore, the axial width of the interior lip 24 of the identification ring 22 and the width of the recess 18 of the terminal plug member 12 should be substantially identical so that there is no gap between the identification ring and the terminal plug member 12 when in fully assembled position as shown in FIGS. 1 and 3, whereby a foreign implement such as a screw driver or the like cannot be utilized to pry the identification ring off of the terminal end of the lead wire 10.

Referring to FIGS. 4 through 6, an alternate embodiment of the invention is shown at the terminal plug end 12 of the lead wire 10 but like numerals are applied corresponding to the same components shown in FIGS. 1-3. In this embodiment of the invention, the identification ring is designated 22a and is shorter than the identification ring 22 shown in FIGS. 1-3. The identification ring 22a has an interiorly threaded portion 28, and the reduced diameter portion 16 of the terminal plug member 12 has an exteriorly threaded portion 30 generally the same width as the threaded portion 28 of the identification ring 22a. As with the interior lip 24 of the identification ring 22 shown in FIG. 2, the interior threaded portion 28 of the identification ring 22 is generally the same width as the recess 18 not only to eliminate any gap between the identification ring and the terminal body member but, in this instance, so that the threaded portion 28 of the identification ring 22a when fully threaded onto the terminal body member is out of threaded engagement with the exteriorly threaded portion 30 to further prevent unintentional removal of the identification ring.

The identification rings 22 and 22a are shown in FIGS. 3 and 6, respectively, in slightly different angular orientations in relation to the terminal body member 12 and lead wire 10 to illustrate the rotational capabilities of the identification rings to facilitate omni-directional reading of the identifying means (described hereinafter) thereon. This is important so that users of the associated electrocardiographic monitoring instruments or machines can easily read the identifying means without twisting the lead wires which oftentimes causes damages thereto which necessitates their replacement.

The identifying means on the identification rings 22, 22a is in the form of raised indicia 32. The raised indicia shown in FIGS. 1 through 6 is in the form of raised letters "LL" corresponding to the left leg of a patient. The terminal plug 20 therefor would be inserted into the appropriate socket on the electrocardiograph monitoring instrument corresponding to the position for receiving a reading from the patient's left leg. It can be seen that with the identification ring being closely associated to and immediately at the end of the terminal end of the lead wire, the likelihood of erroneously positioning the appropriate lead wire into the wrong socket of the electrocardiograph machine is greatly eliminated. The raised indicia 32 is molded with the identification rings 22, 22a so as to be an integral part thereof.

The identification rings 22, 22a shown in FIGS. 1 through 6 are color coded in accordance with the standard color codifications referred to above for the commonly recorded anatomical positions on a patient; namely, LA, RA, LL, RL, VI-6 or others. The identification rings shown in FIGS. 1 through 6 have identifying means in the form of raised letters "LL" corresponding to the left leg of a patient. Thus, the raised letters "LL" would be color coded red in accordance with the conventional codification. The remainder of the identification ring would have the base color white as described above. Preferably, the identification ring and raised letters are fabricated or molded of a thermoplastic material with the raised letters forming an integral part of the identification ring, but with the raised letters being of a different colored material than the remainder of the ring. Each of the other identification rings in any set thereof for use on the limbs of a patient would be white with the raised letters of a different color such as green for the right leg, black for the left arm, and white (white on white) for the right arm. The identification means for the identification rings which are utilized with the terminal plugs for the lead wires 10 corresponding to the anatomical positions on a patient's torso would be fabricated so as to have a common color, namely brown, with the torso positions, e.g., VI-6, comprising raised indicia having the colors red, yellow, green, blue, orange, and violet each on the brown colored rings.

Referring to FIGS. 7 through 9, the end of the terminal wire 10 (the right-hand end as viewed in FIG. 1) opposite the terminal plug end of the lead wire has a terminal body member or portion 34 and a strain relief portion 36 protruding outwardly from one side thereof for receiving a lead wire 10. As shown best in FIGS. 7 and 8, the body member has a reduced diameter portion 38 at the top thereof and a peripheral circular recessed portion 40 extending substantially thereabout. The identification means is in the form of an identification cap 42 which has a generally flat top surface 44 with raised indicia 46 protruding upwardly therefrom. The identification cap 42 has an interior lip 48 which is snap fit within the recess 40 of the terminal body member 34 to retain the identification cap onto the terminal body member and prevent unintentional removal therefrom.

As with the rings 22, 22a shown in FIGS. 1 through 6, the outer or side periphery of the identification cap 42 and the adjacent outer periphery of the terminal body member 34 are rounded and flush with each other to preclude any positive gripping means therebetween. In addition, the width of the recess 44 and the lip 48 are substantially the same so as to eliminate any gap between the identification cap and the body member within which a foreign tool such as a screw driver or the like may be inserted to further reduce the possibility of removal of the identification cap once it is properly assembled to the terminal body member 34 on the end of the lead wire 10.

The raised indicia 46 is similar to the raised indicia 32 shown in FIGS. 1 through 6 except, in this instance, the raised indicia is in the form of the letters "RL" corresponding to the right leg of a patient.

As with the identification rings 22, 22a in FIGS. 1 through 6, the identification cap 42 preferably is molded of thermoplastic material or the like with the raised letters 46 being integral therewith. The raised indicia is fabricated of permanent colored material in accordance with the color codification described above for each limb or torso position of a patient and the remainder of the identification cap 42 is fabricated of colored material corresponding to one of the aforementioned base colors; namely, white or brown.

Furthermore, as with the identification rings 22, 22a, the identification cap 42 is readily rotatable to facilitate omni-directional reading of the raised indicia thereon so that a user does not have to twist the terminal body member 34 or the lead wire 10 to read the identification means which oftentimes causes damage or breakage to the lead wire.

The terminal body member 34 is adapted for positioning onto one of the common recorded anatomical positions of a human torso such as by conventional means including tape, suction cups or the like, which are not shown in the drawings.

It should be pointed out that although the identification means shown and described herein and the various embodiments thereof are particularly useful with electrocardiographic monitoring instruments, the novel features and advantages of the disclosed and claimed structure have wide applications, particularly in the medical field.

While in the foregoing specification a detailed description of the invention has been set forth for purposes of illustration, the details herein given may be varied by those skilled in the art without departing from the spirit and scope of the invention as defined by the appended claims.

I claim:

1. Identification means for application to or in combination with the ends of lead wires for electrocardiographic monitoring instruments or the like, comprising:
   a terminal body member secured at one end of a lead wire and having a peripheral recess extending substantially thereabout; and
   an identification member having identifying means corresponding to one of a plurality of commonly recorded anatomical positions, said identification member being sized to be positionable over at least a portion of said terminal body member including said peripheral recess and having an interior lip snap fit within said recess to retain the identification member onto the terminal body member and prevent unintentional removal therefrom.

2. The identification means of claim 1 wherein the outer peripheral surface of said identification member and the adjacent outer peripheral surface of said terminal body member are rounded and flush with each other to preclude any positive gripping means therebetween.

3. The identification means of claim 1 wherein said recess is circular and of uniform cross section to provide for relative rotation between the terminal body member and the identification member to facilitate omni-directional reading of said identifying means.

4. The identification means of claim 1 wherein said identification member is color coded to one of a plurality of standard color codifications corresponding to a plurality of anatomical positions.

5. The identification means of claim 4 wherein said identification member comprises one of a set of differently color coded identification members.

6. The identification means of claim 1 wherein said identifying means comprises raised indicia on said identification member.

7. The identification means of claim 6 wherein said raised indicia is color coded to one of a plurality of standard color codifications corresponding to a plurality of anatomical positions.

8. The identification means of claim 7 wherein said identification member exclusive of said raised indicia also is color coded to different color codifications than said raised indicia.

9. The identification means of claim 1 wherein said terminal body member has a protruding exteriorly threaded portion and said identification member has an interiorly threaded portion for threading onto the exteriorly threaded portion of the terminal body member, said terminal body member having a reduced diameter portion forming said peripheral recess adjacent the inner end of the exteriorly threaded portion thereof for receiving the interiorly threaded portion of said identification member out of threaded engagement therewith.

10. The identification means of claim 1 wherein said terminal body member is adapted for positioning onto the human anatomy with the lead wire extending outwardly from one side thereof, and said identification member is in the form of a cap having an upwardly facing generally flat surface with said identifying means thereon, said surface being in a plane generally parallel to the lead wire.

11. The identification means of claim 10 wherein the outer peripheral surface of said identification member and the adjacent outer peripheral surface of said terminal body member are rounded and flush with each other to preclude any positive gripping means therebetween.

12. The identification means of claim 1 wherein said terminal body member has a terminal plug protruding outwardly therefrom and electrically connected to the lead wire, and said identification member is in the form of a ring positionable over said terminal plug with the plug protruding therethrough.

13. The identification means of claim 12 wherein the outer peripheral surface of said identification member and the adjacent outer peripheral surface of said terminal body member are rounded and flush with each other to preclude any positive gripping means therebetween.

14. Identification means for application to and in combination with the ends of lead wires of electrocardiographic monitoring instruments or the like, comprising:
   a terminal body member secured at one end of a lead wire and having retaining means thereon;
   an identification member positionable onto said terminal body member and having retaining means complementarily engageable with the retaining means of said terminal body member for selectively assembling the identification member to the body member and prevent unintentional removal therefrom; and
   identifying means on said identification member corresponding to one of a plurality of commonly recorded anatomical positions, said identifying means comprising raised indicia on said identification member, said raised indicia being color coded to one of a plurality of standard color codifications corresponding to a plurality of anatomical positions.

15. The identification means of claim 14 wherein said identification member exclusive of said raised indicia also is color coded to different color codifications than said raised indicia.

16. The identification means of claim 14 wherein said identification member comprises one of a set of differently color coded identification members.

17. The identification means of claim 14 wherein the outer peripheral surface of said identification member and the adjacent outer peripheral surface of said terminal body member are rounded and flush with each other to preclude any positive gripping means therebetween.

18. The identification means of claim 17 wherein the retaining means on said terminal body member comprises a circular recess extending substantially about the periphery of the terminal body member, and the complementary retaining means on said identification member comprises an interior lip snap fit within the recess of said terminal body member to retain the identification member onto the terminal body member and prevent unintentional removal therefrom.

19. The identification means of claim 18 wherein said terminal body member has a protruding exteriorly threaded portion and said indicating member has an interiorly threaded portion for threading onto the exteriorly threaded portion of the terminal body member, said terminal body member having a reduced diameter portion forming said peripheral recess adjacent the inner end of the exteriorly threaded portion thereof for receiving the interiorly threaded portion of said indicating member out of threaded engagement therewith.

20. Identification means for application to and in combination with the ends of lead wires of electrocardiographic monitoring instruments or the like comprising:
   a terminal body member secured at one end of a lead wire;
   an identification member positionable onto said terminal body member;
   complementarily engageable retaining means between said terminal body member and said identification member to retain the identification member onto the terminal body member and prevent unintentional removal therefrom; and
   identifying means on said identification member corresponding to one of a plurality of commonly recorded anatomical positions.

21. The identification means of claim 20 wherein said identifying means is color coded to one of a plurality of standard color codifications corresponding to a plurality of anatomical positions.

22. The identification means of claim 21 wherein said identification member exclusive of said raised indicia also is color to different color codifications than said raised indicia.

23. The identification means of claim 21 wherein said identification member comprises one of a set of differently color coded identification members.

24. Identification means for application to and in combination with the ends of lead wires of electrocardiographic monitoring instruments or the like, comprising:
   a terminal body member secured at one end of a lead wire;
   an identification member having identifying means thereon corresponding to one of a plurality of commonly recorded anatomical positions;
   complementarily engageable retaining means on said terminal body member and said identification member for retaining the identfication member onto the terminal body member and prevent unintentional removal therefrom; and
   the outer peripheral surface of said identification member and the adjacent outer peripheral surface of said terminal body member being flush with each other to preclude any positive gripping means therebetween.

25. The identification means of claim 24 wherein said complementarily engageable retaining means between said terminal body member and said identification member provides for relative rotation therebetween to facilitate omni-directional reading of said identifying means on the identification member.

26. The identification means of claim 24 wherein said outer peripheral surfaces of said identification member and said terminal body member are rounded.

* * * * *